United States Patent [19]

Roeder

[11] Patent Number: 4,623,341
[45] Date of Patent: Nov. 18, 1986

[54] FEMININE NAPKIN WITH UNSECURED TOP LAYER

[75] Inventor: Robert J. Roeder, Outagamie County, Wis.

[73] Assignee: Kimberly-Clark Corporation, Neenah, Wis.

[21] Appl. No.: 529,807

[22] Filed: Sep. 6, 1983

[51] Int. Cl.⁴ .............................................. A61F 13/16
[52] U.S. Cl. ............................... 604/385 R; 604/378; 604/366; 604/370
[58] Field of Search ............... 604/385, 366, 370, 379, 604/380, 378

[56] References Cited

U.S. PATENT DOCUMENTS

| | | | |
|---|---|---|---|
| 3,115,877 | 12/1963 | Harwood | 604/374 |
| 3,183,909 | 5/1965 | Roehr | |
| 3,406,689 | 10/1968 | Hicks et al. | |
| 3,430,630 | 3/1969 | Megison et al. | 604/380 |
| 3,528,422 | 9/1970 | Hodas | |
| 3,897,784 | 8/1975 | Fitzgerald | 604/380 |
| 4,046,147 | 9/1977 | Berg | 604/385 |
| 4,182,334 | 1/1980 | Johnson | |
| 4,340,058 | 7/1982 | Pierce et al. | |
| 4,372,309 | 2/1983 | Fowler | 604/368 |

Primary Examiner—John D. Yasko
Assistant Examiner—Sherri E. Vineyard
Attorney, Agent, or Firm—P. A. Leipold; D. L. Traut; J. J. Duggan

[57] ABSTRACT

A combination sanitary napkin and interlabial pad is provided by forming an absorbent layer which tapers at one end and folding the layer over on itself to form a double layer with the top layer designed, due to its reduced width, to engage the labia of the user. The upper layer is moveable with respect to the bottom absorbent layer.

14 Claims, 2 Drawing Figures

FEMININE NAPKIN WITH UNSECURED TOP LAYER

FIELD OF THE INVENTION

This invention relates to sanitary appliances and particularly to a combination sanitary napkin and interlabial pad.

BACKGROUND OF THE INVENTION

Traditionally, all sanitary napkins have suffered from "distortion failures". These failures because napkins are generally not 3-dimensionally shaped and made to continuously dynamically conform to the perineal area of the wearer particularly when the wearer is in motion. Generally the torque forces exerted on the side of the napkin distort the discharge target area on the face of the napkin and may provide a substantial number of napkin failures due to the angle at which menses strikes the distorted surface.

One of the ways to overcome this type of failure, which has so far proven to be commercially unsuccessful has been to add a positioning means to a conventionally constructed sanitary napkin. This positioning means provides a 3-dimensional napkin profile, is absorbent, and is designed to engage the labia. U.S. Pat. No. 3,528,422 is an example of a sanitary napkin with a raised portion designed to engage the labia.

It is felt that in order to design a satisfactory sanitary napkin with an interlabial pad attached, the interlabial component should be moveable with respect to the conventional napkin absorbent layer. This is true because as forces are exerted on the conventional absorbent layer which would tend to distort them, the interlabial portion will remain in place and functioning therefore minimizing the ultimate effects of these distortion forces. U.S. Pat. Nos. 3,183,909; 3,406,689; and 4,340,058 describe napkins which can be thought of as including an interlabial portion which is moveable with respect to the other absorbent components. Each of these patents disclose an absorbent element which forms the interlabial component as a separate element. This means that in each instance the manufacture of these napkins involve the added steps of assembling the various components and positioning them in registry, both of which make the cost of manufacturing such a high volume disposable product too high.

U.S. Pat. No. 4,182,334 discloses a sanitary appliance shaped somewhat like a paper airplane which is designed to be partially moveable with respect to body movement although this appliance which is essentially of unitary construction does not include an interlabial component.

SUMMARY OF THE INVENTION

According to this invention a sanitary napkin with an interlabial pad component is formed from a unitary absorbent layer which is tapered at one extremity. The absorbent is folded over upon itself to form an upper absorbent layer with the tapered end on the upper portion of the absorbent layer designed to engage the labia. While the upper and lower absorbent components are generally in contact, they need not be and the length of the upper absorbent component can be readily adjusted by the user when she positions the sanitary napkin and, also, the upper component will respond to dynamic motion of the wearer and reposition itself relative to the bottom absorbent component. By making the napkin of a single absorbent layer which is folded upon itself, i.e., a unitary absorbent, a sanitary napkin with an interlabial component can be readily and relatively inexpensively mass produced.

DETAILED DESCRIPTION OF THE INVENTION AND THE DRAWINGS

Figure 1:
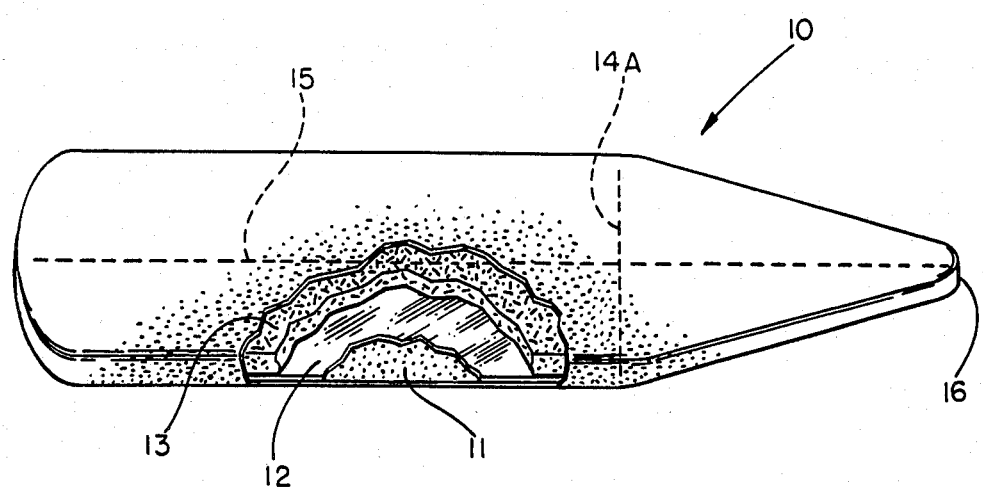
Figure 2:
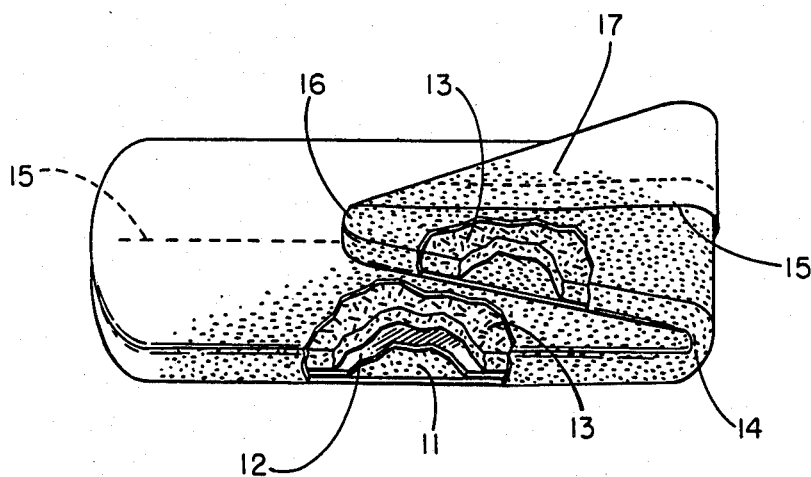

This invention can be better understood by reference to the drawings in which:

FIG. 1 is a plan view partially in cross section of a sanitary napkin-interlabial pad blank according to this invention; and FIG. 2 is a plan view partially in cross section of the combination sanitary napkin and interlabial pad of this invention.

As can be seen from FIG. 1, a sanitary napkin-interlabial pad blank is formed according to the teachings of this invention by attaching a fluid impervious baffle 12 to a portion of the absorbent batt 13. The fluid impervious baffle 12 is designed to extend only along the bottom or garment facing side of the completed-folded napkin-interlabial pad. The absorbent batt 13 with baffle 12 attached is then completely wrapped with a fluid permeable wrap 11 so that the wrap overlaps itself at the bottom of the napkin blank as shown by dotted lines 15. The leading edge 16 of the napkin blank 10 is then folded over to form an upper absorbent layer 17 as can be seen in FIG. 2. The fold occurs along a portion of the napkin blank indicated by dotted lines 14a in FIG. 1 to form the bridge portion 14 in FIG. 2. This folded area may be an area of reduced absorbent thickness or may have a series of score lines or embossing lines or the like to aid in the folding action. If there is any enhancement of the forming of the bridge portion 14 such as by embossment in the bridge region 14a it is desired that the embossment be done in a manner which allows ease of movement of the upper absorbent layer 17 after it has been folded over (in the case of embossments this would mean a plurality of finally spaced sequential embossments in the bridge region 14a. In the preferred embodiment depicted above, the napkin blank is wrapped and then the napkin is folded to form the interlabial portion.

In a less desirable embodiment the napkin can be folded prior to wrapping. The reason this embodiment is less desirable is that there is less potential for movement of the upper layer and the positioning of the upper layer in the labial region will be somewhat more restricted.

What is claimed is:

1. A combination sanitary napkin and interlabial pad comprising:
  (a) a unitary absorbent including,
    (1) a lower absorbent layer;
    (2) a bridge extending upwardly arcuately from said lower absorbent layer;
    (3) an upper absorbent layer forming the interlabial pad portion overlying at least a portion of said lower absorbent layer with said upper layer forming a continuation layer and tapering from the wider portion adjacent said bridge to a leading narrower edge distal from said bridge, said upper absorbent layer being moveable with respect to said lower absorbent layer thereby changing the size relationship between said layers;

(b) a fluid impermeable baffle positioned on the portion of the lower absorbent layer opposite the upper absorbent layer.

2. The napkin according to claim 1 wherein a fluid pervious wrap overlies the upper and lower surfaces of each layer and the inner and outer portions of the bridge.

3. The napkin according to claim 1 wherein the upper layer is wedge-shaped.

4. The napkin of claim 1 wherein said absorbent is covered with a permeable sheet.

5. The napkin of claim 1 wherein the area of said upper absorbent layer is less than that of the lower absorbent layer.

6. The napkin of claim 1 comprising only one bridge.

7. The napkin of claim 1 wherein said fluid impermeable baffle extends along the garment-facing side of said napkin.

8. The napkin of claim 1 wherein said upper absorbent layer is not provided with a fluid-impermeable baffle.

9. The napkin of claim 1 wherein said bridge comprises folded absorbent.

10. The napkin of claim 1 wherein said narrower leading edge distal from the bridge is designed to engage the labia.

11. The napkin of claim 1 wherein said lower absorbent layer and upper absorbent layer comprise a single-absorbent layer which is folded upon itself.

12. A method for making a combination sanitary napkin and interlabial pad comprising:
  (a) positioning a baffle on a defined portion of an absorbent batt said batt generally decreasing in width from one end to the other;
  (b) overwrapping said absorbent layer with a fluid pervious wrap;
  (c) folding said absorbent batt such that the end of decreased width forms an upper absorbent layer movable with respect to the lower absorbent layer, and smaller in area than said lower absorbent layer which is the remainder of said batt with said baffle being positioned on the bottom of said lower absorbent layer wherein said upper absorbent layer decreases in width from the fold to the distal end of said upper absorbent layer.

13. The method of claim 12 wherein said folding is on an embossed line.

14. The method of claim 12 wherein said folding may be adjusted so as to change the size relationship between said layers.

* * * * *